United States Patent
Ogasawara et al.

(10) Patent No.: US 9,127,250 B2
(45) Date of Patent: Sep. 8, 2015

(54) IMMUNOSUPPRESSIVE CELL-CAPTURING MATERIAL AND IMMUNOSUPPRESSIVE CELL-CAPTURING COLUMN

(75) Inventors: Kazumasa Ogasawara, Otsu (JP); Kazuo Teramoto, Otsu (JP); Yuji Ueda, Kyoto (JP); Yasushi Itoh, Otsu (JP); Hirohito Ishigaki, Otsu (JP)

(73) Assignee: Shiga University of Medical Science, Shiga (JP)

( * ) Notice: Subject to any disclaimer, the term of this patent is extended or adjusted under 35 U.S.C. 154(b) by 0 days.

(21) Appl. No.: 14/008,538

(22) PCT Filed: Mar. 27, 2012

(86) PCT No.: PCT/JP2012/057918
§ 371 (c)(1),
(2), (4) Date: Sep. 27, 2013

(87) PCT Pub. No.: WO2012/133399
PCT Pub. Date: Oct. 4, 2012

(65) Prior Publication Data
US 2014/0017667 A1    Jan. 16, 2014

(30) Foreign Application Priority Data
Mar. 29, 2011  (JP) ................. 2011-071475

(51) Int. Cl.
*C12N 5/078* (2010.01)
*B01J 20/26* (2006.01)
*B01J 20/28* (2006.01)
*A61M 1/36* (2006.01)
*A61K 35/14* (2015.01)

(52) U.S. Cl.
CPC ............. *C12N 5/0634* (2013.01); *B01J 20/26* (2013.01); *B01J 20/264* (2013.01); *B01J 20/28042* (2013.01); *A61K 35/14* (2013.01); *A61M 1/3679* (2013.01)

(58) Field of Classification Search
None
See application file for complete search history.

(56) References Cited

U.S. PATENT DOCUMENTS

| 4,839,290 A | 6/1989 | Kaieda et al. |
| 2009/0275874 A1 | 11/2009 | Shimagaki et al. |

FOREIGN PATENT DOCUMENTS

| JP | 56-130160 A | 10/1981 |
| JP | 60-252423 A | 12/1985 |
| JP | 2003-111834 A | 4/2003 |
| JP | 2006-288571 A | 10/2006 |
| JP | 2010-201345 A | 9/2010 |

OTHER PUBLICATIONS

Mahalingam, J. et al. 2014. CD4+ T cells expressing latency-associated peptide and Foxp3 are an activated subgroup of regulatory T cells enriched in patients with colorectal cancer. PLOS One 9(9): 1-9. specif. pp. 1-2.*
Bronte, V. et al. 1999. Unopposed production of granulocyte-macrophage colony-stimulating factor by tumors inhibits CD8+ T cell responses by dysregulating antigen-presenting cell maturation. Journal of Immunology 162: 5728-5737. specif. pp. 5728 and 5734.*
Beyer et al., Regulatory T cells in cancer, Blood 108, 804-811, 2006.
Nakamura et al., TGF4-β1 Plays an Important Role in the Mechanism of CD4•CD25•Regulatory T Cell Activity in Both Humans and Mice, The Journal of Immunology, 172, 834-842, 2004.
Chen et al., Novel CD8• Treg suppress EAE by TGF-β- and IFN-y-dependent mechanisms, European Journal of Immunology, 39, 3423-3435, 2009.
Sinha et al., Proinflammatory S100 Proteins Regulate the Accumulation of Myeloid-Derived Suppressor Cells, The Journal of Immunology, 181, 4666-4675, 2008.
International Search Report dated Jun. 26, 2012 for International application No. PCT/JP2012/057918.

* cited by examiner

*Primary Examiner* — John S Brusca
*Assistant Examiner* — Sharon M Papciak
(74) *Attorney, Agent, or Firm* — Morgan, Lewis & Bockius LLP

(57) ABSTRACT

This invention discloses an immunosuppressive cell-capturing material comprising a molded body that includes: a readily hydrolyzable condensation polymer having an amino group; a poorly hydrolyzable polymer coating the readily hydrolyzable condensation polymer; and a ligand-conjugated poorly hydrolyzable polymer coating the poorly hydrolyzable polymer, wherein the ligand is at least one selected from the group consisting of a $NH_2$ group, a secondary amino group, a tertiary amino group, a polyamine residue, a basic cyclic polypeptide residue, an aminoglycosidic compound residue, chloroquine, primaquine, mefloquine, imiquimod, and nystatin, and wherein the content of the amino group in the molded body is 150 μmol/g or less. The invention also discloses an immunosuppressive cell-capturing column filled with the capturing material.

16 Claims, No Drawings

IMMUNOSUPPRESSIVE CELL-CAPTURING MATERIAL AND IMMUNOSUPPRESSIVE CELL-CAPTURING COLUMN

TECHNICAL FIELD

The present invention relates to an immunosuppressive cell-capturing material for use primarily in medical applications, an immunosuppressive cell-capturing column filled with such a capturing material, and a method for treating and preventing cancer with the capturing material.

BACKGROUND ART

Overcoming cancer is a major challenge of modern medicine. Living organisms are endowed with mechanisms to remove cancer cells and remain free of cancer. However, cancer does occur, and it presumably occurs when immunity weakens from some cause.

It is known that the blood of tumor-bearing mammals has increased levels of immunosuppressive proteins such as TGF-β and interleukin-10. It is thus considered possible to improve immunity and suppress tumor growth if these immunosuppressive proteins could be removed by extracorporeal circulation with an adsorption column. Patent Document 1 reports an adsorbent that adsorbs TGF-β and other immunosuppressive proteins. Patent Document 2 describes enhancing cytocidal activity and preventing spread of tumor to lungs by the extracorporeal circulation of the blood from a tumor-bearing rat using a column filled with an adsorbent adapted to adsorb immunosuppressive proteins such as TGF-β1 and S100A8/A9.

Recent findings suggest that some of the white blood cells in the blood of a tumor-bearing organism are immunosuppressive. Such cells with immunosuppressive activity are identified as $CD4^+CD25^+FoxP3^+$ regulatory T cells (Non-Patent Document 1), $CD4^+$ and $CD8^+$ regulatory T cells expressing latency-associated peptide (hereinafter, simply "LAP") on cell surfaces (Non-Patent Documents 2 and 3), and myeloid-derived suppressor cells such as $Gr1^{high}CD11b^{high}$ (Non-Patent Document 4).

These cells secrete high levels of immunosuppressive proteins such as TGF-β and interleukin-10, and removing these cells is considered important in cancer treatment, probably more so than removing the immunosuppressive proteins.

However, the immunosuppressive cells are not the only cells contained in the blood; blood contains large numbers of other white blood cells that serve to improve immunity. It is indeed not easy to selectively remove only the immunosuppressive cells that account for only about 10% of the total white blood cells. One way of adsorbing only the immunosuppressive cells is to use a bead column immobilizing antibodies against immunosuppressive cells. However, the column needs to be sterilized by heat or radiation in order to be used for treatment. By being protein, the antibodies denature in the sterilization procedure, and lose functions. To date, no method is available that can sterilize protein-immobilized materials, and no column is known that can remove the immunosuppressive cells from blood for treatment.

CITATION LIST

Patent Document

PTD 1: JP-A-2003-111834
PTD 2: JP-A-2010-201345

Non-Patent Document

NPD 1: M. Beyer and J. L. Schultze, Blood 2006:108:804-811
NPD 2: K. Nakamura, A. Kitani, I. Fuss, A. Pedersen, N. Harada, H. Nawata and W. Strober, The Journal of Immunology 2004: 172: 834-842
NPD 3: M. L. Chen, B. S. Yan, D. Kozoriz and H. L. Weiner, European Journal of Immunology 2009:39:3423-3435
NPD 4: P. Sinha, C. Okoro, D. Foell, H. H. Freeze, S. Ostrand-Rosenberg and G. Srikrishna, The Journal of Immunology 2008: 181: 4666-4675

SUMMARY OF INVENTION

Technical Problem

It is accordingly an object of the present invention to provide a non-protein immunosuppressive cell-capturing material for selectively capturing immunosuppressive cells, an immunosuppressive cell-capturing column filled with the capturing material, and a method for treating and preventing cancer with the capturing material.

Solution to Problem

The present inventor conducted various studies to find a method of producing a medical column for selectively capturing the immunosuppressive cells from blood without using antibodies, and found that the foregoing object can be achieved with the use of an aminated polyethylene terephthalate fiber that was made porous by degrading the polymer present on the fiber surface. Specifically, it was found that immunosuppressive cells can be selectively captured with low adsorption to plasma proteins such as albumin when ligands other than a quaternary ammonium group are used and when the amino group is present in low density.

The present invention was completed after further studies on the basis of these findings, and provides an immunosuppressive cell-capturing material, an immunosuppressive cell-capturing column, and a cancer therapeutic and/or preventive method, as follows.

(I) Immunosuppressive Cell-Capturing Material
(I-1) An immunosuppressive cell-capturing material comprising a molded body that includes:
a readily hydrolyzable condensation polymer having an amino group;
a poorly hydrolyzable polymer coating the readily hydrolyzable condensation polymer; and
a ligand-conjugated poorly hydrolyzable polymer coating the poorly hydrolyzable polymer,
wherein the ligand is at least one selected from the group consisting of a $NH_2$ group, a secondary amino group, a tertiary amino group, a polyamine residue, a basic cyclic polypeptide residue, an aminoglycosidic compound residue, chloroquine, primaquine, mefloquine, imiquimod, and nystatin, and
wherein the content of the amino group in the molded body is 150 μmol/g or less.
(I-2) A capturing material according to (I-1), wherein the ligand excludes a quaternary ammonium group.
(I-3) A capturing material according to (I-1) or (I-2), wherein the readily hydrolyzable condensation polymer is polyester or polyurethane.
(I-4) A capturing material according to any one of (I-1) to (I-3), wherein the poorly hydrolyzable polymer is polysulfone, polyetherimide, polyimide, or a derivative thereof.

(I-5) A capturing material according to any one of (I-1) to (I-4), wherein the readily hydrolyzable condensation polymer is polyester, and wherein the poorly hydrolyzable polymer is polysulfone.
(I-6) A capturing material according to (I-1) to (I-5), wherein the immunosuppressive cell is a cell that has a latency-associated protein on a cell surface.
(I-7) A capturing material according to any one of (I-1) to (I-5), wherein the immunosuppressive cell is a cell with up-regulated expression of granulocyte antigen and CD11b antigen.
(II) Immunosuppressive Cell-Capturing Column
(II-1) An immunosuppressive cell-capturing column comprising the capturing material of any one of (I-1) to (I-7) filled therein.
(II-2) A column according to (II-1), wherein the column is used for extracorporeal circulation.
(II-3) A column according to (II-1), wherein the column is used for cell therapy.
(II-4) A column according to any one of (II-1) to (II-3), wherein the column is used for cancer treatment.
(II-5) A column according to any one of (II-1) to (II-3), wherein the column is used for preventing recurrence of cancer after cancer removal surgery.
(III) Cancer Therapeutic and/or Preventive Method
(III-1) A method for treating and/or preventing cancer, the method comprising contacting the blood of a patient to the capturing material of any one of (I-1) to (I-7).

Advantageous Effects of Invention

The capturing material and column of the present invention can selectively capture immunosuppressive cells from blood, and can thus lower the concentration of immunosuppressive cells. The capturing material and column of the present invention have potential application in cancer treatment and cancer recurrence prevention.

Further, the capturing material of the present invention uses a non-protein material, and can be sterilized.

DESCRIPTION OF EMBODIMENTS

The present invention is described below in greater detail.
Immunosuppressive Cell-Capturing Material
The immunosuppressive cell-capturing material of the present invention comprises a molded body that includes:
a readily hydrolyzable condensation polymer having an amino group;
a poorly hydrolyzable polymer coating the readily hydrolyzable condensation polymer; and
a ligand-conjugated poorly hydrolyzable polymer coating the poorly hydrolyzable polymer,
wherein ligand is at least one selected from the group consisting of a $NH_2$ group, a secondary amino group, a tertiary amino group, a polyamine residue, a basic cyclic polypeptide residue, an aminoglycosidic compound residue, chloroquine, primaquine, mefloquine, imiquimod, and nystatin, and
wherein the content of the amino group in the molded body is 150 μmol/g or less.
Configuration of Capturing Material
As used herein, "immunosuppressive cells" means blood cells that suppress the functions of killer cells and helper T cells. Specific examples include $LAP^+CD4^+$ regulatory T cells and $LAP^+CD8^+$ regulatory T cells having LAP on cell surfaces, and cells having up-regulated expression of granulocyte antigen and CD11b, specifically $Gr1^{high}CD11b^{high}$ cells. These cells can be observed by flow cytometry. Typically, $LAP^+CD4^+$ regulatory T cells and $LAP^+CD8^+$ regulatory T cells account for 0.2% to 15% of their respective T cell subsets in peripheral blood, though the number depends on the individual organism.

As used herein, "selective capturing" means that the proportion of the immunosuppressive cells in blood or a blood cell mixture passed through a column filled with the capturing material decreases after the passage through the column, and that the proportion of the immunosuppressive cells in the captured cells increases after the passage through the column. Preferably, the capturing material of the present invention has the ability to capture LAP-positive T cells and make its proportion 0.7 or less, particularly 0.5 or less of the proportion in a $CD4^+T$ or $CD8^+T$ cell subset after the blood is contacted to the capturing material at a blood/capturing material weight ratio of 20.

The porous capturing material can be obtained through the polyamine treatment of a readily hydrolyzable condensation polymer such as polyethylene terephthalate after coating the polymer surface with a poorly hydrolyzable polymer. The pores present in the vicinity of the capturing material surface are what are left after the polymer chains are pulled out. The pores are thus greater than the size of the polymer molecule, and suited for capturing polymers. Further, because the pores are formed by the aminolysis of the readily hydrolyzable condensation polymer with polyamine, the polymer on the pore surface has an amino group.

The mechanism of selective capturing can be assumed as follows. The LAP on the immunosuppressive LAP-positive T cells has the property to bind to the polyleucine structure, and the polyethylene terephthalate as the capturing material has an aromatic nucleus and an ester group. Such a chemical structure appears to be similar to the polyleucine structure in terms of size, hydrophobicity, and polarity; further, since LAP has phosphoric acid groups present on the side sugar chains, it presumably has an affinity to amino acids.

The readily hydrolyzable condensation polymer used in the present invention may be, for example, a polymer that has an ester bond or a urethane bond (—O—CONH—) on the main chain, and that can be processed into a mechanically strong molded body. Such polymers can hydrolyze under mild conditions. Polyester and polyurethane are examples of such polymers. Polyester is particularly preferred for its high hydrolysis reactivity, high mechanical strength, and high processibility, in addition to being readily available as a premolded product. Specific preferred examples of polyester include polylactic acid, polyglycolic acid, polyethylene terephthalate, and polybutylene terephthalate, of which polyethylene terephthalate is particularly preferred. The polymer molecular weight is not particularly limited, as long as it allows the polymer to be molded. For moldability, the preferred polymer molecular weight is typically 10,000 to 1,000,000, particularly 20,000 to 200,000.

As used herein, "molded body" means a molded body that includes the readily hydrolyzable condensation polymer having an amino group, the poorly hydrolyzable polymer, and the ligand-conjugated poorly hydrolyzable polymer, and may include other polymer components and the like. In an embodiment of the molded body of the present invention, the surface of the readily hydrolyzable condensation polymer having an amino group is coated with the poorly hydrolyzable polymer, and the surface of the poorly hydrolyzable polymer is coated with the ligand-conjugated poorly hydrolyzable polymer. The term "coat" as used herein means both coating the whole polymer, and coating a part of the polymer.

The form of the molded body of the present invention is not particularly limited, and may be appropriately selected from various forms depending on the intended use; the examples of the forms include a fiber, a nonwoven fabric, a film, a hollow fiber, a powder particle, and higher processed products of these.

As used herein, "having an amino group" encompasses an amino group directly attached to the polymer, and an amino group attached to the polymer via a spacer molecule.

The poorly hydrolyzable polymer used in the present invention means a polymer that hardly undergoes hydrolysis with the readily hydrolyzable condensation polymer, and that is soluble in an organic solvent. Particularly preferred is a polymer that can withstand the conditions of gamma sterilization and autoclaving, preferably with an ability to form a film, because it improves the mechanical stability of the processed product. Specific examples of the poorly hydrolyzable polymer include aromatic polysulfone polymers, such as polysulfone consisting of bisphenol A and diphenyl sulfone -{(p-$C_6H_4$)—$SO_2$-(p-$C_6H_4$)—O-(p-$C_6H_4$)—$C(CH_3)_2$-(p-$C_6H_4$)—O}$_n$—, poly(p-phenyleneethersulfone)-{(p-$C_6H_4$)—$SO_2$-(p-$C_6H_4$)—O-(p-$C_6H_4$)—O}$_n$—, and -{(p-$C_6H_4$)—$SO_2$-(p-$C_6H_4$)—O-(p-$C_6H_4$)—$C(CF_3)_2$-(p-$C_6H_4$)—O}$_n$—), and polyetherimides, polyimides, and derivatives thereof. Polysulfone is particularly preferred because it is low cost, and has high processibility and high mechanical strength, which makes it possible to form a strong film and makes the material suitable for medical applications. Polysulfone is also preferred because it allows functional groups to be easily introduced. Of these polymers, polymers that dissolve in non-chlorinated and noncarcinogenic solvents such as tetrahydrofuran, dimethyl sulfoxide, and N-methylpyrrolidone are particularly preferred from the standpoint of preventing environmental pollution, and maintaining health and safety at work. The polymer molecular weight is not particularly limited, as long as it allows the polymer to be molded. For moldability, the preferred polymer molecular weight is typically 10,000 to 5,000,000, particularly 20,000 to 200,000.

Particularly preferred as the poorly hydrolyzable polymer is one that has a reactive functional group on the side chain to form a chemical bond with an amino group. The performance of the capturing material can be improved when the poorly hydrolyzable polymer has a ligand that determines the capturing capability and specificity.

Examples of the reactive functional group include a chloromethyl group, a haloacetamide methyl group, and an acid halide, an acid anhydride, or an ester of a carboxyl group. A chloroacetamide methyl group, an iodoacetamide methyl group, and a bromoacetamide methyl group are particularly preferred from the balance between reactivity and process stability.

The ligand for the poorly hydrolyzable polymer of the present invention is needed to exhibit the capture function, and one or more functional groups are selected according to intended use, for example, from a $NH_2$ group, a secondary amino group, a tertiary amino group, a polyamine residue, a basic cyclic polypeptide residue, and an aminoglycosidic compound residue.

Specific preferred examples include amino groups, including a $NH_2$ group, secondary amino groups such as an N-methyl-amino group, and an N-butyl-amino group, and tertiary amino groups such as an N,N-dimethylamino group, and an N-methyl-N-butylamino group; polyamines such as diethylenetriamine, triethylenetetramine, and tetraethylenepentamine; basic cyclic polypeptides such as polymyxin B, and colistin; and aminoglycosidic compounds such as amikacin, astromicin, isepamicin, arbekacin, tobramycin, kanamycin, dibekacin, streptomycin, gentamicin, netilmicin, and bekanamycin. Chloroquine, primaquine, mefloquine, imiquimod, and nystatin are also preferred.

The ligands with a plurality of amino groups, such as diethylenetriamine and a cyclic polyamino compound also serve as crosslinking groups for the poorly hydrolyzable polymer. Such crosslinking groups are useful for improving the heat resistance and solvent resistance in post-processes, and promoting pore formation.

For medical safety, it is desirable to increase the cell selectivity of the capturing material of the present invention. To this end, it is generally desirable to lower the basicity and the density of the amino group. The adsorbability for plasma proteins such as albumin should be maintained as low as possible when blood is directly processed and brought back to the body as in extracorporeal circulation. Particularly, cytokine release and necrosis as might occur when the captured cells in the capturing material are stimulated by the amino group of the capturing material must be avoided to ensure medical safety. From this perspective, a quaternary ammonium group is excluded from the ligands used for the poorly hydrolyzable polymer. The amino group content in the molded body of the present invention is preferably 150 µmol or less, more preferably 110 µmol or less, particularly preferably 1 to 110 µmol per gram. In the present invention, the amino group content is the value determined by the amino group quantification method described in Examples.

Patent Document 2 (JP-A-2010-201345) in Examples 1 to 3 uses a quaternary ammonium group as the ligand, and the content of the amino group in the adsorbent is 357 µmol/g in Example 4, and 413 µmol/g in example 5. As evidenced above, the porous adsorbent disclosed in Examples of Patent Document 2 differs from the capturing material of the present invention. The porous adsorbent of Patent Document 2 also differs from the capturing material of the present invention in protein adsorbability, which is high in the porous adsorbent of Patent Document 2, and is low in the capturing material of the present invention.

The capturing material of the present invention can selectively capture immunosuppressive cells from a cell mixture of a wide variety of blood cells. Further, because the capturing material of the present invention does not contain a protein component, it can be used pathogen-free with the maintained functions after sterilization procedures such as autoclaving and radiation sterilization.

Capturing Material Producing Method

In an exemplary method of producing the capturing material of the present invention, the readily hydrolyzable condensation polymer is partially degraded by treating the polymer under basic conditions either directly or after coating the polymer surface with the poorly hydrolyzable polymer, and the degraded product is extracted to form a porous structure having an amino group.

The coating of the polymer with the poorly hydrolyzable polymer may be performed by dipping the readily hydrolyzable condensation polymer in a solution of the poorly hydrolyzable polymer, and evaporating the solvent. Another method takes advantage of the temperature-dependent solubility difference. Specifically, the readily hydrolyzable condensation polymer is dipped in a 50 to 70° C. solution of the poorly hydrolyzable polymer, and the poorly hydrolyzable polymer is allowed to gradually deposit and coat the readily hydrolyzable condensation polymer upon cooling. The latter method enables uniform coating, and has the economical advantage, because it does not require an apparatus for evaporating and collecting the solvent. Covering the poorly hydrolyzable polymer with the ligand-conjugated poorly hydrolyzable polymer produces a more desirable capturing material, as specifically described below.

First, a commercially available polyethylene terephthalate nonwoven fabric is heated at 105° C. for 20 min in a 0.5 weight % dimethyl sulfoxide solution of diethylenetriamine to wash and roughen the fiber surface (pretreatment step). After water washing and drying, the resulting nonwoven fabric is dipped in a tetrahydrofuran solution containing chloroacetamide methylpolysulfone (percentage substitution 10 mol %) in 10% of the fiber weight, and the tetrahydrofuran is evaporated to obtain a poorly hydrolyzable polymer-coated product (primary coating step). The coated product is then dipped in a 1 weight % hydrous (20 weight %) dimethyl sulfoxide solution of diethylenetriamine, and heated at 80° C. for 1 hour to obtain a porous molded product (pore forming step). The porous molded product is dipped in a 0.2 weight % dimethyl sulfoxide solution of chloroacetamide methylpolysulfone (percentage substitution 100 mol %), heated at 40° C. for 30 min, and dried after being taken out of the solution and washed three times with dimethyl sulfoxide. The product is then heated at 40° C. for 1 hour in a 1 weight % dimethyl sulfoxide solution of diethylenetriamine, and washed with ethanol and water to obtain the capturing material of the present invention (secondary coating step). Capturing materials with a variety of functions can be obtained by using various ligands in place of the diethylenetriamine.

In the primary coating step, a binding reaction occurs between the surface amino group of the polyethylene terephthalate fiber, and the chloroacetamide methyl group of the coated polymer. Without the primary coating, the porous structure does not stabilize, and the extent of pore formation remains low, resulting in poor mechanical strength. Preferably, the poorly hydrolyzable polymer used for coating is dissolved in a low-boiling-point solvent such as tetrahydrofuran, because it makes it easier to evaporate and remove the solvent. The poorly hydrolyzable polymer is coated in preferably 0.1 to 50 weight % of the readily hydrolyzable polymer. Typically, the coating amount is preferably 5 to 20 weight %, though the extent of pore formation increases with increased coating amounts.

The readily hydrolyzable condensation polymer is chemically treated with amine in the pore forming step. The amine is preferably polyamine, particularly preferably diethylenetriamine. Reducing the amount of diethylenetriamine increases the molecular weight of the degraded product oligomer, and produces larger pores. The solubility of the oligomer differs for different solvents, and the pore size and occurrence heavily depend on the selection of solvent. Porosity is believed to increase with solvents that dissolve larger oligomers. However, poor solvents for the poorly hydrolyzable polymer need to be selected, because the coated polymer may fall off when the poorly hydrolyzable polymer dissolves in solvent. From this perspective, it is preferable to use hydrous dimethyl sulfoxide as the solvent. The water content in dimethyl sulfoxide is appropriately selected according to intended use, and is typically 0.1 to 50 weight %, preferably 5 to 20 weight %. The reaction temperature is a temperature lower than the glass transition point. Preferably, the reaction temperature is typically from room temperature to 100° C., particularly room temperature to 80° C., because excessively high reaction temperatures may lower the strength of the molded body.

The secondary coating step after the pore formation is performed to introduce a new ligand. Another purpose is to protect the newly exposed surface of the readily hydrolyzable condensation polymer after the pore forming step. Because the readily hydrolyzable condensation polymer is readily hydrolyzable, coating the surface with the poorly hydrolyzable polymer stabilizes the structure both chemically and physically, making the product preferred for use in medical applications. When the polymer used for the secondary coating is a ligand-conjugated polymer, the cell capturing function and the cell activating function characteristic of the ligand can be imparted.

Immunosuppressive Cell-Capturing Column

The immunosuppressive cell-capturing column of the present invention is a column filled with the immunosuppressive capturing material.

When the capturing material of the present invention has a form of a fiber or a nonwoven fabric, the capturing material of the present invention is filled in the column in a fill density of preferably 50 to 400 mg/cm$^3$, particularly preferably 150 to 300 mg/cm$^3$. With these ranges, the cell capturing efficiency and selectivity, and the pressure drop in the passage of a fluid fall within an appropriate range. Red blood cells hemolyze under increased pressure drop. Hemolysis, in particular, is contraindicated in extracorporeal circulation. Pressure drop has a positive correlation with fill density and blood flow rate. A blood flow rate of at least 30 mL/min is required in humans if the extracorporeal circulation were to be finished in 2 hours, and the pressure drop needs to be 100 mmHg or less to prevent hemolysis of red blood cells.

When used as an extracorporeal circulation column, the column of the present invention can selectively capture the immunosuppressive cells from blood, and can lower the concentration of the immunosuppressive cells. White blood cells prepared from the blood treated with the column of the present invention, and white blood cells treated with the column of the present invention after being isolated in advance have enhanced CTL activity. The column of the present invention can thus be used also for the cell therapy of diseases such as cancer.

The container filled with the capturing material of the present invention may be made of, for example, glass, plastic, and stainless-steel. The size of the container is appropriately selected according to intended use.

The column of the present invention can selectively capture immunosuppressive cells, and can thus be used also for treating viral diseases and cancer, and preventing recurrence of cancer after cancer removal surgery. When used for cancer treatment, the column of the present invention would be useful for enhancing the therapeutic effect of whatever therapy conducted with the column of the present invention, including, for example, surgical therapy, radiation therapy, anticancer drug therapy, activated white blood cell therapy, and vaccine therapy, particularly in the prevention of metastasis and recurrence.

EXAMPLES

The present invention is described below in greater detail using Examples. It should be noted that the present invention is in no way limited by the following Examples.

The methods used in Examples for the measurement of amino group content, the cell surface antigen assay, the preparation of tumor-bearing rats, extracorporeal circulation of rat blood, and the preparation of murine splenic cells and peripheral blood mononuclear cells followed the following procedures, unless otherwise stated.

1. Measurement of Amino Group Content

A sample (0.1 g) was dipped in a 0.1 M solution of picric acid in 70% ethanol (10 mL), and gently shaken for 2 hours. The sample was then washed with 70% ethanol solution until the yellow color of the washing solution disappeared. Then, the sample was dipped in 10 to 50 mL of a 1 weight % solution of diethylamine in 70% ethanol to elute picric acid. The picric acid concentration was then determined from 320 nm absorbance, and the amino group content per gram was obtained by dividing the adsorbed amount by the accurate sample weight.

2. Cell Surface Antigen Assay

Cell surface antigen assay was performed with a FACS-Caliber (Becton, Dickinson and Company). The cell surface staining antibodies used are phycoerythrin-labeled anti-human LAP, FITC-labeled anti-rat CD4, APC-labeled anti-rat CD4 (Becton, Dickinson and Company), FITC-labeled anti-rat granulocyte marker, APC-labeled anti-rat CD8, phycoerythrin-labeled anti-rat CD3 (e-Bioscience), and APC-labeled anti-rat CD11b/c (Biolegend).

3. Preparation of Tumor-Bearing Rats

Preparation of KDH-8 Cells

4-Dimethylaminoazobenzene-induced hepatoma cells KDH-8 (Satoshi Yano, The Hokkaido Journal of Medical Science, Vol. 68, 5, 654-664 (1993)) were subcultured in complete medium (RPMI1400 medium: fetal bovine serum 10 volume %, 2-mercaptoethanol 50 μg/L, streptomycin 50 μg/mL, penicillin-G50 unit/mL). The cells were transferred to a new 150-cm$^2$ culture flask, and cultured for 4 days before use.

Preparation of Tumor-Bearing Rats 1 to 10×10$^5$ cancer cells KDH-8 were suspended in 0.5 mL of PBS(−), and inoculated subcutaneously into the back of WKAH/Hkm rats (male, 8 to 16 weeks of age) to prepare tumor-bearing rats.

4. Extracorporeal Circulation of Rat Blood

Preparation of Extracorporeal Circulation Column

The capturing material (0.3 g) was charged into a polypropylene cylindrical column (inner diameter 1 cm, inner volume 2 mL) to fabricate an extracorporeal circulation column. After sterilizing the column and the circuit by passing 70% alcohol, 40 mL of heparin-added physiological saline (5 unit/mL) was passed at a rate of 2 mL/min as a pretreatment immediately before extracorporeal circulation.

Extracorporeal Circulation

Tumor-bearing rats of 300 to 400 g body weight were placed under general anaesthesia with Nembutal, and cannulated in the artery and vein of the left thigh. Blood was removed from the artery, and returned into the vein through the extracorporeal circulation column using a microtube pump. The blood was extracorporeally circulated at a flow rate of 2 mL/min for 1 hour. Heparin was continuously administered in 100 units/hour throughout the extracorporeal circulation.

5. Preparation of Murine Splenic Cells and Peripheral Blood Mononuclear Cells

Under anaesthesia with Nembutal, the rats were bled to death from abdominal aorta, and the spleen was removed. The spleen was finely crushed in complete medium, and the cells were collected. The collected cells were treated with a hyposmolar solution to hemolyze and remove red blood cells. The resulting cells were suspended in complete medium to obtain a splenic cell suspension.

Peripheral blood was diluted with the same amount of physiological saline, and the diluted solution was layered on the same amount of a lymphocyte separation solution 1077 (Wako Pure Chemical Industries, Ltd.). After being centrifuged at 800 g×20 min, the mononuclear cell layer was collected, and treated with a hyposmolar solution to hemolyze the red blood cells.

Example 1

Preparation of Poorly Hydrolyzable Polymer 1

A mixed solution of nitrobenzene (20 mL) and sulfuric acid (40 mL) was cooled to 0° C., and 2.6 g (0.02 mol) of N-hydroxymethyl-2-chloroacetamide was added and dissolved at a temperature of 0 to 10° C. The solution was added to a nitrobenzene solution (88.4 g: 0.2 mol/1600 mL) of UDEL polysulfone P3500 while being thoroughly stirred. After being further stirred at 20° C. for 2 hours, the reaction mixture was placed in large excess amounts of cold methanol to precipitate polymer. The precipitate was extracted with methanol until there was no nitrobenzene odor, and dried to obtain a polymer (90.0 g). The polymer was dissolved in 2 L of dimethylformamide, and purified by being reprecipitated in large excess amounts of methanol. The polymer dissolved in dimethylformamide, dimethyl sulfoxide, and tetrahydrofuran. The product polymer was dissolved in chloroform, and cast onto a glass plate to produce a film. The presence of an amide group was confirmed by absorption at 3290-3310, 1670, 1528 cm$^{-1}$ from the infrared absorption spectrum of the film. The measured $^1$HNMR spectrum of deuterated chloroform solution revealed that the percentage substitution as the proportion of the area of the methylene group hydrogen (2H)-derived peak (4.22 ppm) of the benzyl group of the amidemethyl group with respect to the area of the isopropylidene group hydrogen (6H)-derived peak (1.66 ppm; singlet) of the polysulfone main chain was 10%.

Preparation of Poorly Hydrolyzable Polymer 2

A mixed solution of nitrobenzene (130 mL) and sulfuric acid (270 mL) was cooled to 0° C., and 13.6 g (0.13 mol) of N-hydroxymethyl-2-chloroacetamide was added and dissolved at a temperature of 0 to 10° C. The solution was added to a nitrobenzene solution (44.2 g: 0.1 mol/500 mL) of UDEL polysulfone P3500 while being thoroughly stirred. After being further stirred at 20° C. for 2 hours, the reaction mixture was placed in large excess amounts of cold methanol to precipitate polymer. The precipitate was extracted with methanol until there was no nitrobenzene odor, and dried to obtain a polymer (62.0 g). The polymer was dissolved in 1 L of dimethylformamide, and purified by being reprecipitated in large excess amounts of methanol. The polymer dissolved in dimethylformamide and dimethyl sulfoxide, but not in tetrahydrofuran. Elemental analysis: N, 2.1%; Cl: 4.5%. The presence of an amide group was confirmed by 3290-3310, 1670, 1528 cm$^{-1}$ absorption in the infrared absorption spectrum of the potassium bromide pellet. The percentage substitution was found to be 100% as determined from the $^1$HNMR spectrum of the deuterated dimethyl sulfoxide solution of the polymer in the same manner as for the poorly hydrolyzable polymer 1.

Synthesis of Capturing Material: Pretreatment

A polyethylene terephthalate fiber nonwoven fabric (density 48 mg/cm$^3$; Japan Vilene; 88.2 g) was dipped in 2 L of a 0.5 weight % solution of diethylenetriamine in dimethyl sulfoxide, and heated at 105° C. for 20 min. A pretreated nonwoven fabric-1 (87.2 g) was obtained after water washing and drying. The amino group content was 1 μmol/g.

Synthesis of Capturing Material: Coating with Poorly Hydrolyzable Polymer

The poorly hydrolyzable polymer 1 (6 g) previously prepared was dissolved in 800 mL of tetrahydrofuran, and the pretreated nonwoven fabric-1 (40 g) previously prepared was dipped in the solution. The whole was left unattended for 24 hours, and the tetrahydrofuran was evaporated to obtain a primary coated nonwoven fabric-1 (46 g).

Synthesis of Capturing Material: Extraction

The primary coated nonwoven fabric-1 (20 g) was dipped in a solution of diethylenetriamine (20 mL), water (60 mL), and dimethyl sulfoxide (320 mL), and heated for 2 hour in a 75° C. water bath. After being water washed, the nonwoven fabric was extracted 6 times with 60° C. hot water, and dried to obtain a porous nonwoven fabric-1 (19 g). The amino group content was 56 µmol/g.

Synthesis of Capturing Material: Secondary Coating

The poorly hydrolyzable polymer 2 (2 g) previously prepared was dissolved in 200 mL of dimethyl sulfoxide to prepare a 0.2 weight % solution. The porous nonwoven fabric-1 (10 g) previously prepared was dipped in the solution, and heated at 50° C. for 1 hour. The nonwoven fabric was taken out of the solution, and washed three times with dimethyl sulfoxide. The fabric was dipped in 200 mL of dimethyl sulfoxide containing 5 g of diethylenetriamine, and heated in a 40° C. bath for 1 hour. Out of the solution, the nonwoven fabric was washed with ethanol, water washed, and vacuum dried to obtain a diethylenetriaminated nonwoven fabric (capturing material-1 of the present invention; 9.6 g). The amino group content was 62 µmol/g.

Example 2

Synthesis of Capturing Material: Secondary Coating

Polymyxin B (500 mg) was dissolved in 150 mL of 10 weight % hydrous dimethyl sulfoxide to produce a polymyxin solution. The poorly hydrolyzable polymer 2 (2 g) previously prepared was dissolved in 200 mL of the dimethyl sulfoxide to obtain a 1 weight % solution. The porous nonwoven fabric-1 (10 g) previously prepared was dipped in the solution, and heated at 40° C. for 1 hour. The nonwoven fabric was taken out of the solution, and washed three times with dimethyl sulfoxide. The fabric was then dipped in the polymyxin solution, and heated in a 40° C. bath for 1 hour after adding 1 mol sodium hydroxide aqueous solution (5 mL). Out of the solution, the nonwoven fabric was washed with ethanol, water washed, and vacuum dried to obtain a polymyxin nonwoven fabric (capturing material-2 of the present invention; 9.4 g). The amino group content was 55 µmol/g.

Example 3

Synthesis of Capturing Material: Secondary Coating

Primaquine.phosphoric acid (750 mg) was dissolved in 150 mL of 10 weight % hydrous dimethyl sulfoxide to produce a primaquine solution. The poorly hydrolyzable polymer 2 (2 g) previously prepared was dissolved in 200 mL of the dimethyl sulfoxide to obtain a 1 weight % solution. The porous nonwoven fabric-1 (10 g) previously prepared was then dipped in the solution, and heated at 40° C. for 1 hour. The nonwoven fabric was taken out of the solution, and washed three times with dimethyl sulfoxide. The fabric was dipped in the primaquine solution, and heated in a 40° C. bath for 1 hour. Out of the solution, the nonwoven fabric was washed with ethanol, water washed, and vacuum dried to obtain a primaquine nonwoven fabric (capturing material-3 of the present invention; 9.6 g). The amino group content was 48 µmol/g.

Test Example 1

Capturing Ability Evaluation Test-1

$10 \times 10^5$ cancer cells KDH-8 were inoculated subcutaneously into the back of a WKAH/Hkm rat (male, 12 weeks of age). Using 500 units of heparin, blood (10 mL) was collected from the carotid artery of the tumor-bearing rat (body weight 354 g, tumor size 26 mm×21 mm). Splenic cells were prepared from the spleen, and suspended in a complete medium to prepare a cell suspension containing $500 \times 10^4$ splenic cells/mL.

The capturing material (100 mg) was charged into a 10-mL syringe barrel, and a 23 gauge injection needle was fitted after passing complete medium. After passing the splenic cell suspension (10 mL) and complete medium (10 mL), the eluate was centrifuged to make the volume 10 mL. The cells were counted, and the proportion of the LAP-positive cells in the $CD4^+T$ cells was determined with a flow cytometer. The results are presented in Table 1. As Comparative Example 1, a polyethylene terephthalate fiber nonwoven fabric was used after washing.

TABLE 1

| | Capturing material | Cell concentration ($\times 10^4$ cells/mL) | Percentage of LAP-positive cells in $CD4^+T$ cells (%) | Percentage decrease of LAP-positive cells (%) |
|---|---|---|---|---|
| Ex. 1 | Capturing material 1 of the present invention | 383 | 2.18 | 44.1 |
| Ex. 2 | Capturing material 2 of the present invention | 346 | 2.71 | 30.5 |
| Ex. 3 | Capturing material 3 of the present invention | 366 | 1.56 | 60.0 |
| Com. Ex. 1 | PET fiber nonwoven fabric | 355 | 4.24 | −8.7 |
| Com. Ex. 2 | Untreated cell suspension | 500 | 3.90 | 0 |

As shown in Table 1, the proportion of the LAP-positive cells in $CD4^+T$ cells decreased with the capturing materials of the Examples, despite that the percentage cell reduction did not differ greatly. As demonstrated above, the capturing material of the present invention selectively captures $LAP^+CD4^+T$ cells. The polyethylene terephthalate fiber nonwoven fabric captured cells but with no selectivity.

Test Example 2

Capturing Ability Evaluation Test-2

The capturing material (100 mg) was charged into a 10-mL syringe barrel, and a 23 gauge injection needle was fitted after passing complete medium. After passing the blood obtained in Test Example 1 (3 mL) and complete medium (5 mL), the red blood cells were removed from the eluate, and the proportion of the LAP-positive cells in the $CD4^+T$ cells was determined with a flow cytometer. The results are presented in Table 2. As Comparative Example 1, a polyethylene terephthalate fiber nonwoven fabric was used after washing.

TABLE 2

| | Capturing material | Percentage of LAP-positive cells in $CD4^+T$ cells (%) | Percentage decrease of LAP-positive cells (%) |
|---|---|---|---|
| Ex. 1 | Capturing material 1 of the present invention | 0.17 | 65.3 |
| Ex. 2 | Capturing material 2 of the present | 0.25 | 49.0 |

TABLE 2-continued

|  | Capturing material | Percentage of LAP-positive cells in CD4+ T cells (%) | Percentage decrease of LAP-positive cells (%) |
|---|---|---|---|
| Ex. 3 | Capturing material 3 of the present invention | 0.22 | 55.1 |
| Com. Ex. 1 | PET fiber nonwoven fabric | 0.53 | −8.2 |
| Com. Ex. 2 | Untreated cell suspension | 0.49 | 0 |

As shown in Table 2, the proportion of the LAP-positive cells in CD4+T cells decreased with the capturing materials of the Examples, demonstrating that the capturing material of the present invention selectively captures LAP+CD4+T cells from the whole blood. On the other hand, it can be seen that the polyethylene terephthalate fiber nonwoven fabric had no selectivity.

Test Example 3

Treatment Experiment-1

$1 \times 10^5$ cancer cells KDH-8 were inoculated subcutaneously into the back of a WKAH/Hkm rat (male, 14 weeks of age). The tumor size increased to 13 mm×13 mm after 3 weeks. After collecting blood (1 mL) from the artery of the tumor-bearing rat (body weight 400 g), the rat was subjected to extracorporeal circulation for 1 hour with a column filled with the capturing material-1 of the present invention (0.3 g). After the extracorporeal circulation procedure, the whole blood was collected to obtain a 15-mL blood sample. A physiological phosphate buffer (50 mL) with 500 units of heparin was passed in reverse direction through the extracorporeal circulation column to collect the adhered cells. A total of $25 \times 10^6$ cells were collected.

The blood before and after the extracorporeal circulation and the adhered cells were assayed for surface antigen. The results are presented in Table 3.

TABLE 3

|  | Before extracorporeal circulation | After extracorporeal circulation | Collected adhered cells |
|---|---|---|---|
| Percentage of LAP-positive cells in CD4+ T cells (%) | 1.31 | 0.43 | 4.62 |
| Percentage of LAP-positive cells in CD8+ T cells (%) | 1.75 | 0.33 | 2.67 |
| Percentage of cells with up-regulated granulocyte marker expression in CD11bc+ cells (%) | 77.2 | 59.1 | 93.6 |
| CD11bc+/CD3+ T ratio | 0.63 | 0.41 | 17.54 |

As shown in Table 3, the proportion of the LAP-positive cells decreased to 33% of the initial value in CD4+T cells, and to 19% of the initial value in CD8+T cells after the extracorporeal circulation with the capturing materials of the present invention, and the adhered cells contained increased numbers of LAP-positive cells. These results demonstrate that the capturing material of the present invention selectively captures the LAP-positive T cells from the whole blood. It can also be seen that the proportion of the probable immunosuppressive cells with the up-regulated granulocyte marker expression in the CD11bc+ cells also decreased after the extracorporeal circulation.

Test Example 4

Treatment Experiment-2

$2 \times 10^5$ cancer cells KDH-8 were inoculated subcutaneously into the back of a WKAH/Hkm rat (male, 13 weeks of age). The tumor size increased to 23 mm×22 mm after 20 days. After collecting blood (1 mL) from the artery of the tumor-bearing rat (body weight 350 g), the rat was subjected to extracorporeal circulation for 1 hour with a column filled with the capturing material-1 of the present invention (0.3 g). After the extracorporeal circulation procedure, the whole blood was collected to obtain a 15-mL blood sample. A physiological phosphate buffer (50 mL) with 500 units of heparin was passed in reverse direction through the column used for the extracorporeal circulation, and the adhered cells were collected. A total of $28 \times 10^6$ cells were collected.

The blood before and after the extracorporeal circulation and the adhered cells were assayed for surface antigen. The results are presented in Table 4.

TABLE 4

|  | Before extracorporeal circulation | After extracorporeal circulation | Collected adhered cells |
|---|---|---|---|
| Percentage of LAP-positive cells in CD4+ T cells (%) | 5.06 | 1.97 | 12.30 |
| Percentage of LAP-positive cells in CD8+ T cells (%) | 0.56 | 0.11 | 6.73 |
| CD11bc+/CD3+ T ratio | 2.55 | 0.63 | 55.73 |

As shown in Table 4, the proportion of the LAP-positive cells decreased to 39% of the initial value in CD4+T cells, and to 20% of the initial value in CD8+T cells after the extracorporeal circulation with the capturing material of the present invention, and the adhered cells contained increased numbers of LAP-positive cells. These results demonstrate that the capturing material of the present invention selectively captures the LAP-positive T cells from the whole blood.

Test Example 5

CTL Suppression Experiment $1 \times 10^5$ cancer cells KDH-8 were inoculated subcutaneously into the back of a WKAH/Hkm rat (male, 10 weeks of age). The tumor size increased to 10 mm×10 mm after 20 days. The whole blood was collected from the rat, and the mononuclear cells were removed to prepare a cell suspension containing $5 \times 10^6$ cells/mL. The adhered cells obtained by desorbing the cells captured in the column in Test Example 4 were adjusted to $5 \times 10^6$ cells/mL.

3 μL of a 5(6)-carboxy fluorescein succinimidyl ester dimethylsulfoxide solution (5 mg/mL) was added to a 1-mL suspension of KDH-8 cells in physiological phosphate buffer ($1 \times 10^7$ cells/mL), and the mixture was heated at 37° C. for 15 min. The reaction was stopped by addition of complete medium (10 mL), and the cells were suspended in complete medium after being washed to prepare a cell suspension containing $1 \times 10^5$ labeled cancer cells/mL.

The labeled cancer cell suspension (17 μL) and the mononuclear cell suspension (500 μL) were added to each well of a 24-well culture plate, and the adhered cell suspension (0, 50, 100, 150, or 200 μL) was added. The cells were cultured in a 37° C. carbon dioxide gas incubator for 40 hours, and analyzed with a flow cytometer. The propidium iodide-positive cells in the FL-1-positive cells were identified as killed cancer cells, and the negative cells as viable cancer cells, and the killer activity (CTL activity) was calculated. The experiment was conducted with n=4. The results are presented in Table 5.

TABLE 5

| Percentage of added adhered cells (%) | CTL activity (%) |
|---|---|
| 0 | 32.3 |
| 10 | 27.6 |
| 20 | 23.5 |
| 30 | 20.1 |
| 40 | 18.1 |

It can be seen from the table that the CTL activity decreased in proportion to the amount of the added adhered cells. The result demonstrates that the cells captured by the column are highly immunosuppressive.

Test Example 6

Cell Treatment Experiment $1 \times 10^5$ cancer cells KDH-8 were inoculated subcutaneously into the back of four WKAH/Hkm rats (male, 12 weeks of age). The tumor size increased to 10 to 13 mm after 3 weeks. Two of the tumor-bearing rats were subjected to extracorporeal circulation for 1 hour using a column filled with the capturing material-1 (0.3 g) of the present invention. After the extracorporeal circulation procedure, the whole blood was collected, and two blood samples (15 mL each) were obtained. After separating the mononuclear cells by centrifugation, the red blood cells were removed by hemolysis. As a result, a total of $6 \times 10^7$ mononuclear cells (treated rat PBMC) was obtained. A total of $6 \times 10^7$ mononuclear cells (tumor-bearing rat PBMC) was obtained from the blood of the remaining two rats. Concurrently, blood was collected from three WKAH/Hkm rats (male, 15 weeks of age), and a total of $7 \times 10^7$ mononuclear cells (normal rat PBMC) was obtained in the same manner.

$1 \times 10^5$ cancer cells KDH-8 were inoculated subcutaneously into the back of nine WKAH/Hkm rats (male, 9 weeks of age). The treated rat PBMC, tumor-bearing rat PBMC, or normal rat PBMC ($3 \times 10^7$ cells) were dispersed in 0.5 mL of physiological phosphate buffer, and injected to each of the three rats in three groups at the same site. Table 6 represents the results of tumor growth observation. Rats with a tumor size exceeding 40 mm were euthanized under deep anesthesia.

TABLE 6

| | Tumor size: mm | | | | | | | | |
|---|---|---|---|---|---|---|---|---|---|
| | Treated rat PBMC Rat # | | | Tumor-bearing rat PBMC Rat # | | | Normal rat PBMC Rat # | | |
| Days after inoculation | 1 | 2 | 3 | 4 | 5 | 6 | 7 | 8 | 9 |
| 14 | 0 | 0 | 0 | 0 | 5 | 5 | 0 | 0 | 0 |
| 21 | 0 | 0 | 0 | 13 | 15 | 15 | 12 | 12 | 13 |
| 28 | 0 | 0 | 0 | 25 | 30 | 30 | 22 | 25 | 25 |
| 35 | 0 | 0 | 0 | 52 | 58 | 63 | 43 | 50 | 45 |
| 42 | 0 | 0 | 0 | | | | | | |

It can be seen from Table 6 that the peripheral blood mononuclear cells of the rats after the extracorporeal circulation with the capturing material of the present invention completely suppressed establishment of cancer cells, whereas the peripheral blood mononuclear cells of the untreated rats completely lacked the suppressing effect.

Example 4

Synthesis of Capturing Material: Coating with Poorly Hydrolyzable Polymer

The poorly hydrolyzable polymer 1 (3.00 g) previously prepared was dissolved in 300 mL of dimethyl sulfoxide at 60° C., and the pretreated nonwoven fabric-1 (19.04 g) previously prepared was dipped in the solution. After being left unattended for 1 hour, the whole was cooled to 20° C. over the course of 8 hours while being shaken. The solution was transparent, and the polymer was not suspended. After removing dimethyl sulfoxide by centrifugation, the nonwoven fabric was water washed, and dried to obtain a primary coated nonwoven fabric-2 (21.25 g).

Synthesis of Capturing Material: Extraction

The primary coated nonwoven fabric-2 (20.8 g) was dipped in a solution of diethylenetriamine (15 mL), water (65 mL), and dimethyl sulfoxide (320 mL), and heated in a 70° C. water bath for 3 hours. The nonwoven fabric was extracted with 50° C. hot water until the washing solution turned transparent. The fabric was then dried to obtain a porous nonwoven fabric-2 (20.0 g). The amino group content was 115 µmol/g.

Synthesis of Capturing Material: Secondary Coating

The poorly hydrolyzable polymer 2 (1 g) previously prepared was dissolved in 200 mL of dimethyl sulfoxide to prepare a 0.5 weight % solution. The porous nonwoven fabric-2 (10 g) previously prepared was dipped in the solution, and heated at 50° C. for 1 hour. The nonwoven fabric was taken out of the solution, and washed three times with dimethyl sulfoxide. The fabric was then dipped in 200 mL of a 50% dimethyl sulfoxide solution containing 5 g of diethylenetriamine, and heated in a 40° C. bath for 1 hour. Out of the solution, the nonwoven fabric was water washed, and vacuum dried to obtain a diethylenetriaminated nonwoven fabric (capturing material-4 of the present invention; 9.8 g). The amino group content was 105 µmol/g.

Test Example 7

Cancer Recurrence Suppression Experiment

Protein Adsorption Test

Human AB serum (Dainippon Sumitomo Pharma Co., Ltd.) was filtered through a 0.22 µm filter, and each capturing material (50 mg) of the present invention was dipped in the serum (2 mL). The whole was gently shaken at 37° C. for 2 hours. The albumin and TGF-β1 concentrations in the serum were then measured. The results are presented in Table 7.

There was hardly any decrease in albumin and TGF-β concentrations, showing that the adsorbent of the present invention has low protein adsorbability. The albumin concentration was determined by using the BCG method (Clinical Chemistry 1972:18:1537-1538), and the TGF-β1 was measured with an ELISA kit (R & D). The initial values were 3.3 mg/dL for albumin, and 8.5 ng/mL for TGF-β1.

TABLE 7

| | Percentage removal: % | |
| --- | --- | --- |
| | TGF-β1 | Albumin |
| Capturing material 1 of the present invention | 7.1 | 0.2 |
| Capturing material 2 of the present invention | 2.0 | 0.1 |
| Capturing material 3 of the present invention | 0.0 | 0.1 |
| Capturing material 4 of the present invention | 0.0 | 0.0 |

$5 \times 10^4$ cancer cells KDH-8 were inoculated subcutaneously into the right back of a WKAH/Hkm rat (male, 12 weeks of age). The tumor size increased to 3 mm after 35 days. The rat was subjected to extracorporeal circulation for 1 hour using a 1.6-mL cylindrical column filled with the capturing material-4 (0.3 g) of the present invention (fill density 190 mg/cm$^3$). Blood (1 mL) was collected before and after the extracorporeal circulation, and these blood samples and the collected adhered cells were assayed for surface antigen. The results are presented in Table 8.

TABLE 8

| | Before extracorporeal circulation | After extracorporeal circulation | Collected adhered cells |
| --- | --- | --- | --- |
| Percentage of LAP-positive cells in CD4$^+$ T cells (%) | 3.34 | 1.03 | 5.59 |
| Percentage of LAP-positive cells in CD8$^+$ T cells (%) | 0.37 | 0.22 | 1.61 |
| CD11bc$^+$/CD3$^+$ T ratio | 0.74 | 0.67 | 33.60 |

As shown in Table 8, the proportion of the LAP-positive cells decreased to 31% of the initial value in CD4 T cells, and to 59% of the initial value in CD8$^+$T cells after the extracorporeal circulation with the capturing material-4 of the present invention, and the collected adhered cells contained increased numbers of LAP-positive cells. These results demonstrate that the capturing material-4 of the present invention selectively captures the LAP-positive T cells from the whole blood.

Cancer Recurrence Suppression Experiment $5 \times 10^4$ cancer cells KDH-8 were inoculated subcutaneously into the right back of eight WKAH/Hkm rats (male, 12 weeks of age). The tumor size increased to 10 to 13 mm after 7 weeks. After surgically removing the tumors from all rats under anesthesia with Nembutal, $1 \times 10^5$ cancer cells KDH-8 were reinoculated subcutaneously into the left back of each rat. Immediately, randomly selected four tumor-bearing rats were subjected to extracorporeal circulation for 1 hour with a 1.6-mL cylindrical column filled with the capturing material-4 (0.3 g) of the present invention (fill density 190 mg/cm$^3$). The survival times of the rats were then compared with those of rats that had no extracorporeal circulation. After the surgery, 0.1% gentamicin sulfate ointment was applied to the incision site, and the incision was sutured to prevent infection. The results are presented in Table 9.

TABLE 9

| Rat # | Tumor size at removal (mm) | Presence or absence of extracorporeal circulation | Survival time (days) |
| --- | --- | --- | --- |
| 11 | 11 | Absent | 19 |
| 12 | 13 | Absent | 21 |
| 13 | 10 | Absent | 19 |
| 14 | 11 | Absent | 20 |
| 15 | 11 | Present | >200 |
| 16 | 12 | Present | >200 |
| 17 | 12 | Present | 45 |
| 18 | 10 | Present | 27 |

As shown in Table 9, the rats that had no extracorporeal circulation survived for 20 days on average. In contrast, two of the four rats that had the extracorporeal circulation with the capturing material of the present invention had no tumor recurrence, and the cancer cured completely. The remaining two survived for 45 days and 27 days, respectively. These results demonstrate that the capturing material of the present invention has a prominent cancer recurrence suppressing effect.

The invention claimed is:

1. A molded body comprising:
    a first polymer having an amino group;
    a second polymer coating the first polymer; and
    a third polymer that is conjugated to at least one ligand and coats the second polymer,
    wherein the first polymer is more hydrolyzable than the second and third polymers,
    the at least one ligand is selected from the group consisting of a NH$_2$ group, a secondary amino group, a tertiary amino group, a polyamine residue, a basic cyclic polypeptide residue, an aminoglycosidic compound residue, chloroquine, primaquine, mefloquine, imiquimod, and nystatin, and
    the total content of amino groups in the molded body is 150 μmol/g or less.

2. The molded body according to claim 1, wherein the third polymer is not conjugated to a quaternary ammonium group.

3. The molded body according to claim 1, wherein
    the first polymer is polyester or polyurethane, and
    each of the second and third polymers independently is polysulfone, polyetherimide, polyimide, or a derivative thereof.

4. A column comprising the molded body of claim 1.

5. A method of treating cancer, the method comprising contacting blood of a patient to the molded body of claim 1.

6. A method of removing an immunosuppressive cell from blood, comprising contacting blood to the molded body of claim 1, and capturing an immunosuppressive cell from the blood.

7. The molded body according to claim 1, wherein the first polymer is a condensation polymer.

8. The molded body according to claim 1, wherein
    the first polymer comprises polyester or polyurethane, and
    each of the second and third polymers independently comprises polysulfone, polyetherimide, or polyimide.

9. A method of removing an immunosuppressive cell from a patient, comprising extracorporeally circulating blood from a patient through the column of claim 4.

10. A method of lowering concentration of an immunosuppressive cell in a patient, comprising extracorporeally circulating blood from the patient through the column of claim 4, and returning the blood to the subject.

11. The method according to claim 10, wherein the immunosuppressive cell is a cell that has latency-associated protein on the cell surface.

12. A method of enhancing cytotoxic T lymphocyte (CTL) activity in a patient, comprising extracorporeally circulating blood from the patient through the column of claim 4, and returning the blood to the patient.

13. A method of treating cancer in a subject in need of treatment of cancer, comprising extracorporeally circulating blood from the subject through the column of claim 4, and returning the blood to the subject.

14. A method of treating cancer in a subject in need thereof, comprising passing blood of the subject through the column of claim 4, and lowering concentration of an immunosuppressive cell in the blood upon the passing of the blood through the column.

15. A method of lowering concentration of an immunosuppressive cell in blood of a subject after tumor removal surgery, comprising extracorporeally circulating blood from the subject through the column of claim 4, and returning the blood to the subject.

16. A method of removing an immunosuppressive cell from blood, comprising passing blood through the column of claim 4, and capturing an immunosuppressive cell in the column.

* * * * *